United States Patent [19]

Sakata et al.

[11] Patent Number: 5,352,583
[45] Date of Patent: Oct. 4, 1994

[54] HUMAN TISSUE PLASMINOGEN ACTIVATOR-HUMAN PLASMINOGEN ACTIVATOR INHIBITOR COMPLEX IMMUNOASSAY AND KIT THEREFOR

[75] Inventors: Yoichi Sakata, Utsunomiya; Kazuhiko Itoh, Iwakuni; Shuichiro Hino, Iwakuni; Ryoichi Hasegawa, Iwakuni; Naomi Okamoto, Iwakuni; Atsushi Noro, Hino; Toshinobu Murakami, Kokubunji, all of Japan

[73] Assignee: Teijin Limited, Japan

[21] Appl. No.: 687,867

[22] PCT Filed: Oct. 2, 1990

[86] PCT No.: PCT/JP90/01269

§ 371 Date: Jun. 3, 1991

§ 102(e) Date: Jun. 3, 1991

[87] PCT Pub. No.: WO91/05257

PCT Pub. Date: Apr. 18, 1991

[30] Foreign Application Priority Data

Oct. 2, 1989 [JP] Japan .................................. 1-255307
Oct. 3, 1989 [JP] Japan .................................. 1-256995

[51] Int. Cl.$^5$ ............................................. G01N 33/53
[52] U.S. Cl. .................................... 435/7.4; 435/7.92; 435/13; 435/962; 436/527; 436/531; 436/548; 436/69; 530/388.25; 530/389.3
[58] Field of Search ................ 435/7.4, 7.9, 7.92–7.95, 435/13, 810, 962.963, 975; 436/527, 531, 548, 69, 808; 530/388.25, 389.3

[56] References Cited

U.S. PATENT DOCUMENTS 4,148,869 4/1979 Deaton .......................... 435/7.4 X

FOREIGN PATENT DOCUMENTS 0339302 11/1989 European Pat. Off. .
8600413 1/1986 World Int. Prop. O. ............ 435/13
8900005 1/1989 World Int. Prop. O. ............ 435/13

OTHER PUBLICATIONS

R. Vogt et al., "Quantitative differences among various proteins as blocking agents for ELISA microtiter plates", in Journal of Immunological Methods, vol. 101, pp. 43–50 (1987).

Y. Takada et al., "Measurements of the Concentration of Free-Plasminogen Activator, Inhibitor (PAI-1) and Its Complexes with Tissue Plasminogen Activator", Chemical Abstract 109(25):225318.

Takada et al. *Thrombosis Research*, vol. 55, No. 5; 601-610 "Plasma levels of t-P A, free PAI-1 and a complex of t-PA with PAI-1 in human males and females at various ages" (1989).

J. Amiral et al., *Thrombosis Research*, Supplement VIII; 99–113, "Measurement of tPA and tPA––PAI-1 complexes by Elisa, using monoclonal antibodies: clinical relevance" (1988).

*Primary Examiner*—Carol A. Spiegel
*Attorney, Agent, or Firm*—Wenderoth, Lind & Ponack

[57] ABSTRACT

A kit for the immunological assay of the human tissue plasminogen activator-human plasminogen activator inhibitor complex in a human specimen, which kit comprises (i) a monoclonal antibody (first antibody) against a human plasminogen activator inhibitor linked onto an insoluble solid carrier having a specular surface, (ii) a polyclonal antibody (second antibody) against a human tissue plasminogen activator labelled by an enzyme, (iii) a substrate and a reaction-discontinuing agent for the assay of the enzyme activity, (iv) a diluent, and (v) a detergent containing a nonionic surfactant having an HLB (Hydrophile Lipophile Balance) value of at least 16, and a method for the immunological assay of the above complex and a method for the immunological assay of the active human plasminogen activator inhibitor, respectively in a human specimen using this kit.

6 Claims, 3 Drawing Sheets

HUMAN TISSUE PLASMINOGEN ACTIVATOR-HUMAN PLASMINOGEN ACTIVATOR INHIBITOR COMPLEX IMMUNOASSAY AND KIT THEREFOR

Detailed Description of the Invention a. Industrial Applicable Field

This invention relates to the immunological assay of the human tissue plasminogen activator-human plasminogen activator inhibitor complex in a human specimen. More detailedly, the invention relates to an immunological assay method for assaying with a high sensitivity and stably the amount of the complex in a human specimen, and a kit therefor.

The symbols used in the present description have the following meanings unless otherwise defined.

tPA: Human tissue plasminogen activator

PAI: Human plasminogen activator inhibitor (Inhibitor against tPA)

tPA-PAI complex: Human tissue plasminogen activator-human plasminogen activator inhibitor complex b. Prior Art Plasmin, an enzyme to dissolve fibrin, is formed from the conversion of plasminogen with a tissue plasminogen activator (tPA). In recent years, it was found that an inhibitor against this human tissue plasminogen activator [human plasminogen activator inhibitor (PAI)] exists in blood vessel endothelial cells, cutaneous cells, platelets, the placenta, etc., and forms without delay a complex with the human tissue plasminogen activator, and thereby inhibits a human tissue plasminogen activator activity (M. Philips et al, Biochem Biophys, Acta, 802, 99–110, 1984, S. Thorsen, Biochem Biophys Acta, 802, 111–118, 1984, T. Wun et al, J, Biol Chem. 262, 3646–3653, 1987, M. A. Sanzo et al, Biochem, 26, 7443–7449, 1987, Y. Sakata et al, J. Biol Chem. 263, 1960–1969, 1988). Further, there has been a clarification of the relationship between the activity value of the plasminogen activator inhibitor (PAI) in the blood and a disease (B. Wiman et al. Scand. J. Clin Lab Invest 45, 43–43, 1985, P. Vague et al, Metabolism 35, 250–253, 1986, A. Hamsten, Lancet 8549,3–8, 1987), and it is suggested that the plasminogen activator inhibitor (PAI) is an important control factor of the initiation mechanism of the blood coagulation fibrinogenolysis system. Therefore, when it is possible to know the concentration of PAI, tPA and the tPA-PAI complex in the blood, there is a large possibility that the abnormality and pathema of the fibrinogenolysis system can be monitored.

Presently, as assay methods for tPA there are methods by sandwich enzyme immunoassay (Japanese Laid-Open Patent Publication No. 174759/1984), kits on the market (Biopool Co., IMULYSE t-PA), etc., and on the other hand as methods for assay PAI there are methods using a radioactive substance (R. R. Schlef et al, J. Lab Clin Med 106, 408, 1985), a sandwich enzyme immunoassay kit using a monoclonal antibody (Biopool Co., IMULYSE PAI-I), etc.

Further, it is said that a very small amount of a tPA-PAI complex exists in the plasma, and as an assay method for this tPA-PAI complex there is an enzyme immunoassay method based on the fluorescence method, wherein a monoclonal antibody against PAI is used as an immobilized antibody, a polyclonal antibody against tPA is used as a labeled antibody and its fragment is labeled with β-galactosidase.

This system to assay the tPA-PAI complex comprises reacting, first, the immobilized monoclonal anti-PAI-1 antibody with a specimen at 30° C. for 3 hours, washing, reacting with the Fab' fragment of the polyclonal anti-tPA labeled with β-galactosidase at 4° C. overnight to complete the immunological logical reaction, decomposing 4-methyl-umbelliferyl galactoside, and assaying the formed 4-methylumbelliferone by the fluorescence method to quantitatively determine to tPA-PAI complex. Such method has problems that the reaction temperatures differ between the two immunological reactions, reaction time is necessary to be overnight and very long, and further a fluorescence photometer, a special measurement apparatus, is used, and thus it has been difficult to make the assay effectively in industrial and clinical aspects.

On the other hand, Amiral et al. propose, as an assay method for a tPA-PAI complex, a method for assaying the tPA-PAI complex using a monoclonal antibody against PAI and a monoclonal antibody against tPA (Thrombosis Research, Supplement VIII; 99–113, 1988). In this method two kinds of monoclonal antibodies are used and the tPA-PAI complex can be assayed with a relatively good sensitivity, but according to the ELISA disclosed in this literature, the assay takes about 5 hours or more in total. Therefore, in order to utilize actually and clinically the assay system wherein these two kinds of monoclonal antibodies are used, it is indispensable to further raise the assay sensitivity, simplify the operation and shorten the operation time.

Problems to be Solved by the Invention

The first object of this invention lies in the provision of an immunological assay method and a kit, whereby the tPA-PAI complex in a human specimen can be assayed in a high sensitivity.

The second object of the invention lies in the provision of a method to assay the tPA-PAI complex in a human specimen by a convenient, clinically usable means.

Another object of the invention lies in the provision of an immunological method and a kit, whereby the tPA-PAI complex in a human specimen can be assayed stably and with a high sensitivity with minimal influence of subjects, assay conditions (time, temperature, etc.), etc.

Still another object of the invention lies in the provision of an assay method for the active PAI in a human specimen.

Still other objects of the invention will further be clarified by the following description.

Means for Solving the Problems

According to studies by the present inventors, it was found that the above objects and advantages of the invention can be accomplished by a kit for the immunological assay of the tPA-PAI complex in a human specimen, which kit comprises (i) a monoclonal antibody (first antibody) against a human plasminogen activator inhibitor linked onto an insoluble solid carrier having a specular surface, (ii) a polyclonal antibody (second antibody) against a human tissue plasminogen activator labeled by an enzyme, (iii) a substrate and a reaction-discontinuing agent for the assay of the enzyme activity, (iv) a diluent, and (v) a detergent containing a nonionic surfactant having an HLB (Hydrophile Lipophile Balance) value of at least 16.

Further, according to studies by the inventors are provided the following immunological assay method for a tPA-PAI and assay method for an active PAI.

Immunological assay method for tPA-PAI (1) A method for the immunological assay of the human tissue plasminogen activator-human plasminogen activator inhibitor complex in a human specimen by (1) contacting the human specimen with a first antibody linked to an insoluble solid carrier, and then contacting a labeled second antibody therewith, or (2) simultaneously contacting a first antibody linked to an insoluble solid carrier, a labeled second antibody and the human specimen, which method comprises (a) using as the first antibody a monoclonal antibody against a human plasminogen activator inhibitor linked onto an insoluble solid carrier having a specular surface, (b) using as the second antibody a polyclonal antibody against a human tissue plasminogen activator labeled with an enzyme, and (c) using as a detergent a detergent containing a nonionic surfactant having an HLB (Hydrophile Lipophile Balance) value of at least 16.

Assay method for an active PAI

In a method which comprises assaying respectively by an immunological assay method based on the sandwich method (A) the human tissue plasminogen activator-human plasminogen inhibitor complex existing in a human specimen, and (B) the human tissue plasminogen activator-human plasminogen inhibitor complex existing in the human specimen to which a human tissue plasminogen activator was added, and assaying the amount of the active human plasminogen activator inhibitor based on the difference of the assay values, a method for the assay of the active human plasminogen activator inhibitor which comprises (a) using as a first antibody a monoclonal antibody against a human plasminogen activator inhibitor linked onto insoluble solid carrier having a specular surface, (b) using as a second antibody a polyclonal antibody against a human tissue plasminogen activator labeled with an enzyme, and (c) using as a detergent a detergent containing nonionic surfactant having an HLB (Hydrophile Lipophile Balance) value of at least 16.

The above inventions are characterizing by (i) using a monoclonal antibody against PAI as a first antibody (immobilized antibody) and an enzyme-labeled polyclonal antibody against tPA as a second antibody in combination, (ii) using as an insoluble solid carrier for the immobilization of the first antibody a solid carrier having a specular surface, namely an extremely smooth surface, and (iii) using a detergent containing a nonionic surfactant having an HLB value of a certain value or more, and the objects of the invention can be accomplished by the synergistic influences of these (i), (ii) and (iii).

Namely, as the synergistic effects of the above (i), (ii) and (iii), the nonspecific adsorption of many proteins existing in the human specimen, particularly tPA, PAI and the like on the solid carrier is inhibited to the utmost, the nonspecific adsorption of the second antibody is inhibited and the specific adsorption thereof is selectively promoted, and thus components unnecessary for the immune reaction can effectively be washed and removed.

Thus according to the invention, tPA-PAI contained in an extremely small amount in a human specimen can be assayed with a high sensitivity, conveniently, precisely and stably, and moreover, practical effects can also be accomplished, i.e., the time required for the assay is sharply shortened compared to usual methods and the use amount of the detergent is reduced.

Further according to the invention, when the immune reaction is carried out by two steps, it is not necessary to set different temperatures in each step and it is readily possible to carry out it at the same temperature, and it is possible to carry out all steps including the immune reaction and the enzymatic reaction in two hours or a shorter time.

Therefore, the immunological assay system in the invention, whereby a human specimen having abnormality in a coagulation fibrinogenolysis activity or a human specimen suspected of having the abnormality can effectively and speedily be assayed, has an extremely large clinical significance.

This invention is described in more detail below.

[A] Preparation and isolation of an antigen

A monoclonal antibody against PAI and a polyclonal antibody against tPA used in the invention can be obtained using an antigen described below.

Namely, as tPA or PAI as an antigen for obtaining these antibodies there can in principle be used either of one of a natural type extracted from a natural material and one of a recombinant type by a gene recombinant technique, but one obtained by a gene engineering method can also be used so long as it has immunological properties equal to the natural type tPA or PAI. Cell culture broths are used by choice as a material from which a natural type tPA or PAI is obtained. Separation and purification can be carried out by a combination of usually used protein separation techniques such as salting out, extraction, centrifugation, ultrafiltration and various chromatographies.

A polyclonal antibody or a monoclonal antibody can be prepared using as an antigen the thus obtained tPA or PAI.

[A]-(1) Preparation of a polyclonal antibody against tPA

A polyclonal antibody against tPA used in the invention can be obtained according to a known method se using the tPA as an antigen. For example, as is described in "Edited by Nippon Seikagaku-kai (Japan Biochemistry Society), Zoku Seikagaku Jikken Koza (Second Series Biochemical Experiment Course), volume 5, pages 1 to 10, Tokyo Kagaku Dojin, 1986", an antiserum is obtained by immunizing an immunizable animal having an antibody production ability such as a guinea pig, rabbit, rat, mouse, goat with tPA by a conventional method and then withdrawing blood. A purified antibody can be obtained from the antiserum by a combination of usually used methods such as salting out, extraction, centrifugation, ultrafiltration and various chromatographies.

[A]-(2) Preparation of a monoclonal antibody against PAI A monoclonal antibody against PAI used in the invention can be obtained by using PAI as an antigen, culturing a hybridoma prepared by a cell fusion method by Köhler and Milstein known per se [G. Köhler and Milstein, Nature (London), 256, 495–497 (1975)] to make it secrete the monoclonal antibody, and separating it from the culture broth. Namely, after the immunization of a mouse with PAI, the spleen cells of this mouse and a mouse myeloma cell are fused to prepare hybridomas. Since the thus obtained hybridomas produce various monoclonal antibodies in accordance with the various fused lymphocytes, a hybridoma producing a desired monoclonal antibody is isolated as a hybridoma cloned by cloning. This cloned hybridoma is cultured in vitro or in the mouse abdominal cavity to make it secrete the monoclonal antibody. The monoclonal antibody against PAI is separated from this culture broth according to conventional methods.

As such a monoclonal antibody against PAI, JTI-1, JTI-2, JTI-3 or JTI-4 can be used as previously proposed by the present applicant and disclosed in European Laid-Open Patent Publication No. 339302. Among them, JTI-3 and JTI-4 are preferred, and JTI-4 is particularly excellent in the invention.

These two monoclonal antibodies JTI-3 and JTI-4 are internationally deposited according to the Budapest Treaty as described below.

A monoclonal antibody JTI-3 against PAI

As for this monoclonal antibody JTI-3 against PAI, the hybridoma producing it was deposited with Fermentation Research Institute, an international deposit organ based on the Budapest Treaty, or Nov. 22, 1988 as FERMp-10405, and thereafter changed to the international deposit on Mar. 2, 1989 (International Deposit No. BP-2317).

This monoclonal antibody JTI-3 against PAI belongs to the subclass IgG$_1$ and has a characteristic of recognizing to an antigenic determination site such that even when tPA was linked to PAI (namely even in a tPA-PAI complex), its linkage to PAI is not inhibited, but when the monoclonal antibody was linked to PAI, the linkage of tPA to PAI is inhibited.

A monoclonal antibody JTI-4 against PAI

As for this monoclonal antibody JTI-4 against PAI, the hybridoma producing it is deposited with the above Fermentation Research Institute, Agency of Industrial Science and Technology, 1-3, Higashi 1-chome, Tsukuba-shi, Ibaraki-Ken 305, Japan, Nov. 22, 1988 as FERMp-10406, and thereafter changed to the international deposit (International Deposit No. Ferm BP-2318) on Mar. 2, 1989.

This monoclonal antibody JTI-4 against PAI belongs to the subclass IgG$_1$ and its linkage to PAI is not inhibited even when PAI is linked to tPA.

[B] Preparation of an assay kit for a tPA-PAI complex

[B]-(1) Preparation of a first antibody

As a first antibody in the invention, it is necessary to use a monoclonal antibody against PAI linked onto an insoluble solid carrier having a specular surface.

By using as this solid carrier one having a specular surface, namely one having an extremely smooth surface, nonspecific adsorption is lowered and the assay sensitivity of the tPA-PAI complex increases.

Heretofore, as insoluble solid carriers for highly sensitive assay, those whose surface area was enlarged by grinding and thereby roughening the surface have been used. Indeed, when the surface is enlarged, there arises a merit of increasing the amount of the immobilized antibody, but there was a demerit that nonspecific adsorption is increased. As a result of studies, the present inventors found based on the assay of a tPA-PAI complex that a solid carrier having a specular surface, namely having a center line average roughness (Ra) of 1.5 μm or less is advantageous for the highly sensitive assay of the tPA-PAI complex because the amount of the antibody fixed thereon is almost equal compared to a solid carrier having a roughened surface, while nonspecific adsorption thereon is remarkably decreased. Although such insoluble solids having a specular surface are limited particularly in material and shape, polystyrene beads and glass beads can for example be mentioned.

The center line average roughness (Ra) means the value of Ra expressed by a micron unit which is given by the following equation when the part of the measurement length l is extracted from the roughness curve in the direction of its center line, and the center line of this extracted part, the direction of longitudinal magnification and the roughness curve are represented by an X axis, a Y axis and y=f(x) respectively, $$Ra = \frac{1}{l} \int_o^l /f(x)/\, dx$$

About this center line average roughness (Ra) description is made JIS B 0601-1982 (Japan), ANSI B 46.1-1979 (USA) and R468-1966 (ISO International Organization for Standardization).

In the following examples of the invention, the surface roughness of the insoluble carriers was measured using a surface roughness tester Surfcom ® produced by TOKYO SEIMITSU CO., LTD.

As monoclonal antibodies against PAI immobilized onto such inactive carriers, there can be mentioned not only the above monoclonal antibody molecules but also their fragments whose antigen likage ability is not lost, e.g. F(ab')$_2$, Fab, Fab', Facb (a half molecule of IgG), etc or derivatives of the antibodies or their fragments whose antigen linkage ability is not lost. As methods to immobilize these antibodies onto insoluble carriers there can be used physical adsorption methods such as, for example, a method which comprises immersing a polystyrene carrier in a solution of such an antibody; ionic bond methods such as a method using, for example, an ion exchange resin or a carrier having an ionizing functional group such as an amine group, carboxylic acid group, sulfonic acid group or phosphoric acid group; covalent bond methods by chemical reactions such as, for example, carboxy-chloride methods, carbodiimide methods, maleic anhydride derivative methods, isocyanate derivative methods, cyanogen bromide-activated polysaccharide methods, diazo methods, active ester methods and carrier linkage methods using cross-linking reagents (as crosslinking reagents there can be mentioned glutaraldehyde, hexamethylene isocyanate, a succinimide-maleimide compound, etc.); and further methods wherein linkage is carried out through a substance having no linkage ability to PAI but capable of binding to the monoclonal antibody by a biological reaction, for example a method using a protein A-bonded carrier, and the like.

[B]-(2) Preparation of a second antibody (labeled antibody)

In the invention, as a second antibody is used an enzyme-labeled polyclonal antibody against tPA. Polyclonal antibodies against tPA or their fragments equal thereto described in the [A]-(1) are labeled using enzymes used for immunological assay methods. As enzymes used for this labeling, there can, for example, be mentioned lysozyme, maleate dehydrogenase, glucose-6-phosphate, dehydrogenase, peroxidaze, glucose oxidase, alkaline phosphatase, luciferase, $\beta$-galactosidase, etc. The linkage between these enzymes and the polyclonal antibodies can be carried out by conventional methods such as glutaraldehyde methods, periodic acid methods and maleimide methods, but maleimide methods are preferably used.

The maleimidation of antibodies and enzymes can be carried out by methods known per se [Edited by Eiji Ishikawa "Koso Meneki Sokutei-ho" (Enzymatic Immunoassay Method), Igaku shoin], for example by using a crosslinking reagent such as succinimdyl 4-(N-maleimidomethyl)cyclohexane carbonate (SMCC), sulfosuccinimidyl 4-(N-maleimidomethyl)cyclohexane carbonate (sulfo SMCC), Succinimidyl metamaleimidobenzoate (MBS) or succinimidyl 6-maleimidohexanoate (EMCS).

Reaction between a polyclonal antibody against tPA or its fragment and a labeling substance can be carried out by reacting the polyclonal antibody maleimidated with an above crosslinking reagent or its fragment with an enzyme to which SH groups were introduced, for example with $\delta$-acetylmercaptosuccinic anhydride, for example at a temperature of 4° to 30° C. and at a molar ratio of the antibody or its fragment to the SH group-introduced enzyme of 1:1 to 1:80 for 1 to 48 hours. In this case, it is preferred to obtain a product wherein the antibody or its fragment is labeled with the labeling substance, chiefly in the rate of one molecule of the latter per one molecule of the former through the sulfur atoms of the former.

[B]-(3) Detergent

In an immunological assay method according to the sandwich method, only by a simple combination of an immobilized antibody (first antibody) and a labeled antibody (second antibody), nonspecific adsorption takes place and a highly sensitive assay system cannot be established. Thus, it is a point for highly sensitive assay to inhibit the nonspecific reaction. For example, although the use of a surfactant in the assay system reduces nonspecific adsorption, not all the surfactants are effective in the tPA-PAI complex assay system.

The present inventors found that when the first antibody and the second antibody are combined as described above, there arises an effect that a particular surfactant does not inhibit the immune reaction in the assay system of the tPA-PAI complex but inhibits only the nonspecific adsorption of substances not involved in the immune reaction and the labeled antibody.

In this invention, it is advantageous for highly sensitive assay to make such a surfactant as an immune activator exist in an immune reaction solution or in a detergent solution. When the immune reaction is a two-step reaction, the surfactant can be made to exist in either reaction but is preferably made to exist in the second reaction.

Surfactants used in the invention are nonionic surfactants having an HLB (Hydrophilic Lipophilic Balance) value of 16 or more.

Surfactants having an HLB below 16 are not preferred because they inhibit the immune reaction as well as nonspecific adsorption.

Nonionic surfactants having an HLB valve of 16 or more include, for example those of the polyoxyalkylene alkyl aryl ether series, the polyoxyalkylene alkyl ether series, the polyoxyalkylene polyhydric alcohol fatty acid ester series, polyoxyethylene polyoxypropylene polyol series, etc., and examples thereof are TRITON TM X-305 (HLB 17.3), TRITON TM X-405 (HLB 17.9), EMULGEN TM 950 (HLB 18.2), EMULGEN TM 985 (HLB 18.9), TWEEN TM 20 (HLB 16.7), PLURONIC TM F68 (HLB 29), TETRONIC TM 707 (HLB >20), etc.

These surfactants can be used alone, or two or more surfactants can be used together, too.

The concentration of the surfactant in the detergent solution or the like is 1 w/w % or less, preferably 0.001% or more and 0.1 w/w % or less.

In the invention, even in a surfactant amount of 0.1 w.w % or less, an excellent washing effect is exerted, foaming at the time of washing is reduced, and as a result problems are diminished that foaming is intense, and thereby the removal of the foam becomes complicated, or its removal becomes incomplete and conversely washing becomes incomplete, and thus such a surfactant amount is preferred.

As a solvent for the nonionic surfactant any solvent can be used so long as it has no bad influence on the assay, and examples thereof are water, physiological saline and buffers such as a phosphate buffer.

[B]-(4) Diluent

As a diluent used in the assay kit and assay method of the invention, any diluent can be used so long as it is usually used in immunological assays. Namely, such a diluent is one having no bad influence on the immune reaction, and for example are chiefly used buffers having a pH in the range of 6.0 to 8.0 such as phosphate buffers, tris hydrochloride buffers and acetate buffers.

[B]-(5) Substrate and reaction-discontinuing agent for enzymatic activity assay

As substrates and reaction-discontinuing agents used in the assay kit and assay method of the invention, there can be used those usually known in immunological assays in accordance with the kind of enzymes as a labeling substance. As examples thereof, examples of substrates of peroxidase are 2,2'-azino-di-[3-ethyl-benzothiazolinesulfonic acid] diammonium salt (ABTS), orthophenylenediamine (OPD), 3,3',5,5'-tetramethylbenzidine (TMB), etc., and examples of reaction-discontinuing agents therefor are $H_2SO_4$, HCl, acetic acid, glycine buffers (pH 10.3), sodium fluoride solutions, etc.

Examples of substrates of alkaline phosphatase are 4-nitrophenyl phosphate, 4-methylumbelliferyl phosphate, NADP, etc.

Examples of substrates of $\beta$-galactosidase are 2-nitrophenyl-$\beta$-D-glactoside, 4-methylumbelliferyl-$\beta$-D-glactoside, etc. Examples of reaction-discontinuing agents therefor are 0.1M $Na_2CO_3$, etc.

[B]-(6) Use of protein

It was found by the research of the present inventors that when, in the assay of the tPA-PAI complex, a protein having a molecular weight of 16,000 to 50,000, preferably 20,000 to 46,000 and an isoelectric point of 1.0 to 5.0, preferably 1.2 to 4.8 is made to exist in the immune reaction solution and the final concentration of this protein in the immune reaction solution is adjusted to 0.02 to 0.9% by weight, nonspecific adsorption is still further inhibited and thus background is remarkably lowered and further high sensitivity is easily obtained. Examples of such substances are casein, $\beta$-casein, $\alpha$-casein, pepsin, ovoglycoproteins, orosomucoid, etc. These proteins can also be used as a mixture thereof. Such a mixture can contain, for example, as main components 10 to 60%, preferably 20 to 50% by weight of such a protein and 30 to 80%, preferably 40 to 60% by weight of a sugar (e.g. lactose), and in addition a fat (e.g. 0.5 to 2% by weight), an ash (e.g. 5 to 12% by weight), water (e.g. 2 to 8% by weight), etc. Skim milk is a typical example of such a mixture. Skim milk contains casein as a protein, and has advantages that it has a better dispersibility in the immune reaction solution, a higher nonspecific adsorption inhibition effect per unit weight of protein and a better preservability (precipitate is slow to be formed) at 4° C., compared to the case where casein is used alone. The source of skim milk used in the invention does not come into question, and what is only required is that it is defatted milk. It is preferred for the attainment of similar high sensitivity to make skim milk exist in the immune reaction solution and adjust its ultimate concentration in the immune reaction solution to 0.002 to 0.8% by weight. In a concentration lower than 0.002% by weight, a sufficient inhibition effect cannot be obtained, while a concentration higher than 0.8% by weight in case of skim milk or 0.9% by weight in case of an above protein inhibits specific reactions and is thus not preferred.

The above protein can be used in the immune reaction solution in the concentrations mentioned above, and can be contained either in the diluent or in the secondary antibody.

[B]-(7) Assay method

Any human specimen can be used as the human specimen in the assay method of the invention so long as it is a usual clinical liquid sample containing a tPA-PAI complex such as, for example, blood in the form of serum or plasma, synovial fluid, lymph fluid, pleural effusion, ascites, amniotic fluid, cellular tissue fluid, bone marrow fluid or urine. Preferred is blood in the form of serum or plasma.

In the assay method of the invention, the amount of the tPA-PAI complex in a human specimen can be assayed in a high sensitivity by using the first antibody and the second antibody in a combination, and either (i) contacting the human specimen with the first antibody linked to an insoluble solid carrier, and after washing contacting the labeled second antibody therewith, or (ii) making the first antibody linked to an insoluble solid carrier, the labeled first antibody, the labeled second antibody and the human specimen exist in a system.

The method (i) is not influenced by tPA even when tPA exists in a human specimen in a high concentration, e.g. in a specimen from a patient to whom tPA was administered for treatment, and thus superior to the method (ii).

Although the immune reaction temperature condition in the assay is not limited so long as it does not denature the proteins as constituents and does not greatly inhibit the immune reaction, the reaction is suitably carried out in general under a temperature condition on the order of 50° C. or less, preferably about 4° to 45° C. taking a time on the order of about 5 minutes to 5 hours, preferably 30 minutes to 3 hours.

For example, when the reaction temperature is a temperature close to body temperature such as 37° C., nonspecific adsorption reaction can greatly be diminished, and it is also one of the characteristics of the present invention system to exert great power for the high sensitization of the assay system.

[C] Assay method of active PAI

The assay method for a tPA-PAI complex by the invention enables the assay of the tPA-PAI complex in a human specimen in an extremely high sensitivity, and thus by the utilization of this method, it becomes possible to assay the amount of the active PAI in the human specimen easily and in a high sensitivity.

As a method for assaying the concentration of an active PAI, there has hitherto been reported by Takada et al. a method utilizing the formation of a tPA-PAI complex by reaction with tPA and PAI [Thrombosis Research vol. 55, pages 285 to 589 (1989)]. According to this method, the reaction of PAI in a specimen with tPA is carried out at 4° C. overnight and the amount of the formed tPA-PAI complex is then assayed.

This method of assaying the tPA-PAI complex is carried out by first carrying out reaction at 30° C. for 3 hours, washing, conducting reaction with a polyclonal antibody tPA.Fab' fragment labeled with $\beta$-galactosidase at 4° C., completing the immune reaction, decomposing 4-methyl-umbelliferylgalactoside, and assaying the formed 4-methylumbelliferone for fluorescence to quantatively determine the tPA-PAI complex. Effective assay thereof in view of industrial and clinical points has been difficult according to such a method because the method utilizes different temperatures in the two immune reactions, time necessary for the assay is two days and very long, and further a fluorescence photometer, a special measurement apparatus is used.

On the other hand according to the invention, the amount of the active PAI in a human specimen can be assayed conveniently and in a short time by adding tPA into the human specimen to react the active PAI with tPA, measuring the amount of the formed tPA-PAI complex and subtracting the amount of the complex in the specimen to which tPA was not added from the above amount.

Effect of the Invention

Thus according to the method of this invention, the tPA-PAI complex in a specimen containing a very small amount of the tPA-PAI complex such as a clinical sample can quantitatively be determined in a high sensitivity and a high accuracy and by a convenient operation.

Further likewise, the amount of the active PAI in a specimen can be assayed in a high sensitivity and a high accuracy, simply and in a short time.

Example

The invention is detailedly described below by examples. The % symbol in the examples denotes weight %.

REFERENCE EXAMPLE

Figure 1:
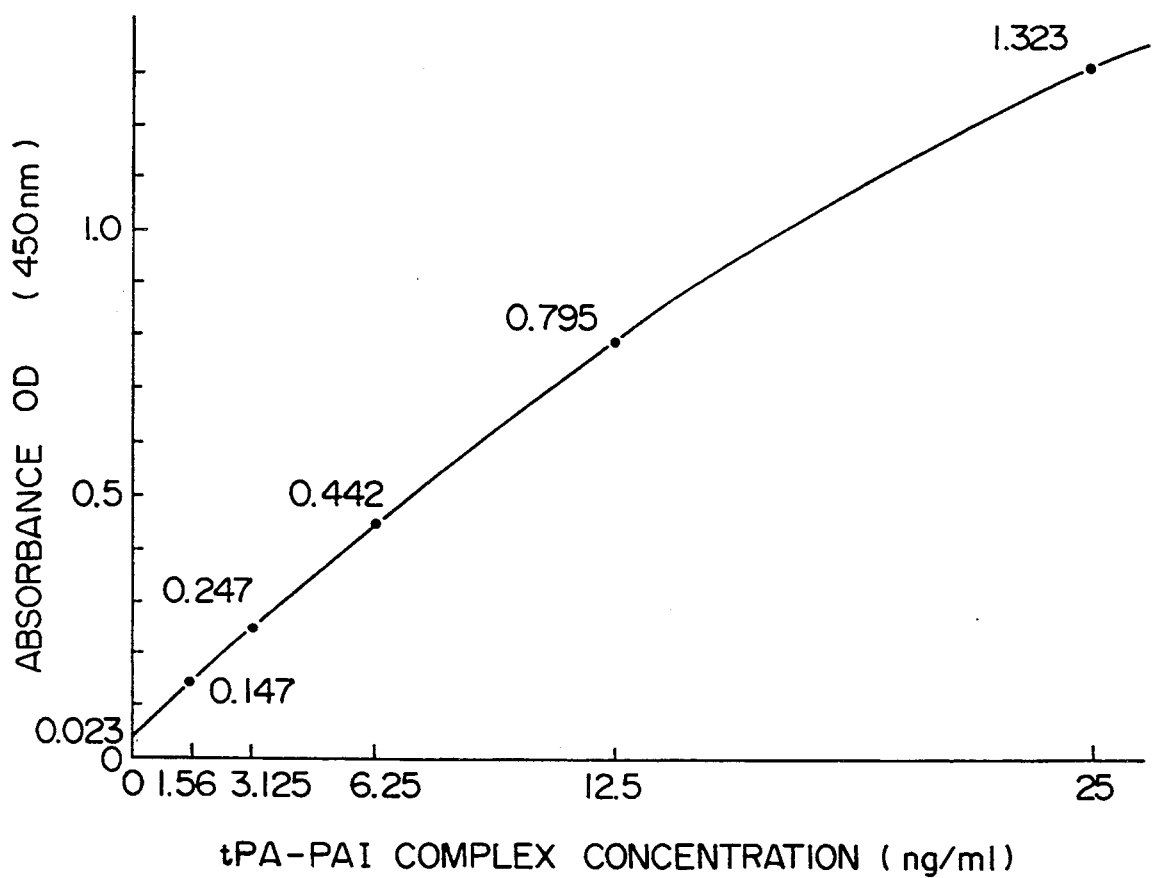
FIG. 1 denotes a calibration curve for the immunological assay of the tPA-PAI complex, and denotes a relationship between the concentration of the tPA-PAI complex and absorbance.

[Preparation of peroxidase-labeled anti-tPA monoclonal antibody Fab' fragment]

The Fab' fragment of a monoclonal antibody against human tissue plasminogen activator (JTA-1; refer to European Laid-Open Patent Publication No. 339302) was prepared according to the method of Nisonov, and linked to peroxidase by a conventional method to obtain peroxidase-labeled Fab' (Editted by Japan Biochemistry Society, Lectures on Biochemistry Experiments, second series, volume 5, pages 109 to 112, Tokyo Kagaku Dojin, 1986). Namely, 40 µg of pepsin was added to 2 ml of a 1.0 mg/ml solution of the monoclonal antibody [0.01M phosphoric acid -0.15M NaCl pH 7.2 (PBS)], and after adjustment to pH 3.7 with a 1M citrate buffer (pH 3.5) the mixture was subjected to digestion and decomposition at 37° C. for one hour. 1N NaOH was added dropwise to the reaction solution to adjust its pH to 8 whereby the reaction was discontinued. This reaction solution was subjected to TSK Gel G-3000SW column (Toso)-HPLC using a 5 mM EDTA-0.1M phosphate buffer (pH 6.0) as an eluent to separate the F(ab')$_2$ fragment having a molecular weight of 100,000.

This was concentrated by an ultrafilter. 200 µl of 0.1M 2-mercaptoethylamine was added thereto and the mixture was subjected to reduction at 37° C. for 2 hours. This reaction solution was concentrated by an ultrafilter and subjected to HPLC in the same manner as in F(ab')$_2$ to separate Fab' having a molecular weight of 50,000 and obtain 1.0 ml of a 1.07 mg/ml Fab' fragment solution.

On the other hand, 6.0 mg of horseradish peroxidase (Toyobo I-C) was dissolved in 0.9 ml of a 1M sodium phosphate buffer (pH 7.0), 60 µl (2.9 mg/80 µl) of a dimethylformamide solution of N-succinimidyl-3-maleimido-methyl-cyclohexane carbonate (Pierce Co., SMCC) was added dropwise thereto, and reaction was carried out at 30° C. for 1 hour. This reaction solution was added to a SEPHADEX ™ G-25 column and a 0.1M sodium phosphate buffer (pH 6.0) was eluted to separate maleimidated peroxidase. 3.2 mg of the thus obtained maleimidated peroxidase and 1.0 mg of the Fab' fragment were reacted at 25° C. for 24 hours, and the reaction mixture was subjected to separation and purification using TSK Gel G-3000 SW column-HPLC (eluent 0.01M PBS) to obtain 0.35 mg of a peroxidase-labeled mouse anti-tPA antibody Fab' fragment having a molecular weight of about 130,000. The linkage molar ratio of the Fab' fragment to peroxidase was 1:2 determined based on the absorbances of the obtained labeled antibody at 280 nm and 403 nm.

EXAMPLE 1

[Preparation of peroxidase-labeled anti-tPA polyclonal antibody]

250 µl of a dimethylformamide solution (10 mg/ml) of N-(m-maleimidobenzoic acid)-N-succinimide ester (MBS, Pierce Co.) was added to 5.0 ml of a PBS solution (1 mg/ml) of goat anti-human tPA antibody (Biopool Co.), and reaction was carried out at a temperature of 25° C. for 30 minutes. Thereafter, gel filtration was carried out using a column packed with SEPHADEX G-25 and a 0.1M phosphate buffer (pH 6.0) to separate the maleimidated polyclonal antibody from the unreacted MBS.

On the other hand, 197 µl of a dimethylformamide solution (60 mg/ml) of S-acetyl succinic anhydride was added to 5.4 ml of a solution (10 mg/ml) of horseradish peroxidase (HRP) in a 0.1M phosphate buffer (pH 6.5). The mixture was subjected to reaction at a temperature of 25° C. for 30 minutes, stirred for 4 minutes after the addition 2.2 ml of a 0.1M Tris buffer (pH 7.0), 4.3 ml of a 1M-hydroxylamine aqueous solution and 0.4 ml of a 0.1M EDTA aqueous solution, and subjected to gel filtration using a column packed with SEPHADEX G-25 and a 0.1M phosphate buffer (pH 6.0) to separate SH lated peroxidase.

The MBS lated antibody and the SH lated peroxidase (5.3 mg) were reacted at 25° C. for 20 hours, and the reaction mixture was subjected to gel filtration using HPLC (TSK Gel G-3000 SW) to obtain 1.9 mg of a peroxidase-labeled anti-tPA polyclonal antibody.

[Preparation of solid antibody]

Polystyrene beads (Immunochemical Co., D-7) having a center line average roughness (Ra) of 1.35 µm were immersed in a solution (20 µg/ml) of the mouse anti-PAI monoclonal anti-PAI antibody (JTI-4) in a 0.1M phosphate citrate buffer (pH 3.0), and the mixture was allowed to stand at 4° C. for 20 hours. The beads were washed with a PBS solution, allowed to stand in a 1% BSA-PBS solution at room temperature for 2 hours, and washed again with a PBS solution to obtain mouse anti-PAI antibody-immobilized beads.

[Making of calibration curve]

A human tPA-PAI complex was diluted with a 0.01M phosphate-0.5M NaCl-2% BSA buffer ( pH 7.2) containing 0.25% skim milk to prepare 25, 12.5, 6.25, 3.125, 1.56, 0 ng/ml solutions. 0.4 ml portions of the solutions of each concentration and the mouse anti-PAI antibody-immobilized beads were placed in small test tubes, and incubation was carried out at 37° C. for 1 hour. The respective kinds of beads were washed twice with a washing solution containing 0.05% TWEEN 20 in PBS.

A solution containing 1 µg/ml the peroxidase-labeled tPA polyclonal antibody was prepared using the antibody and a PBS-0.05% TWEEN 20 solution. 0.4 ml portions of the solution were placed in the above small test tubes, followed by incubation at 37° C. for 30 minutes. After three times washing with the washing solution, 0.4 ml portions of a 2.5 mM $H_2O_2$-0.025% 3,3',5,5'-tetramethylbenzidine 0.1M phosphate citrate (pH 4.0) solution, a substrate solution for peroxidase, were added, and color was developed at 37° C. for 30 minutes. The color development was stopped with 1N sulfuric acid and absorbance at 450 nm was measured.

The calibration curve is shown in FIG. 1.

EXAMPLE 2

[Comparison between the peroxidase labeled anti-tPA monoclonal antibody and the anti-tPA polyclonal antibody]

Figure 2A:
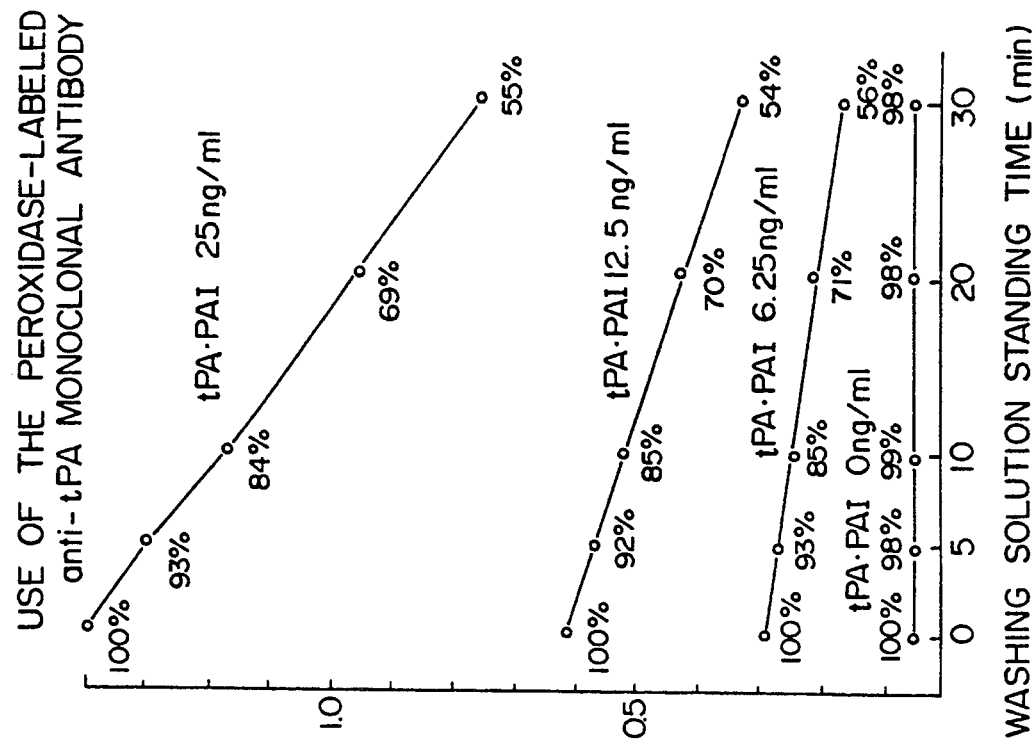
FIGS. 2a and b denotes a relationship between the washing time and absorbance in the immunological assay of the tPA-PAI complex.
Figure 2B:
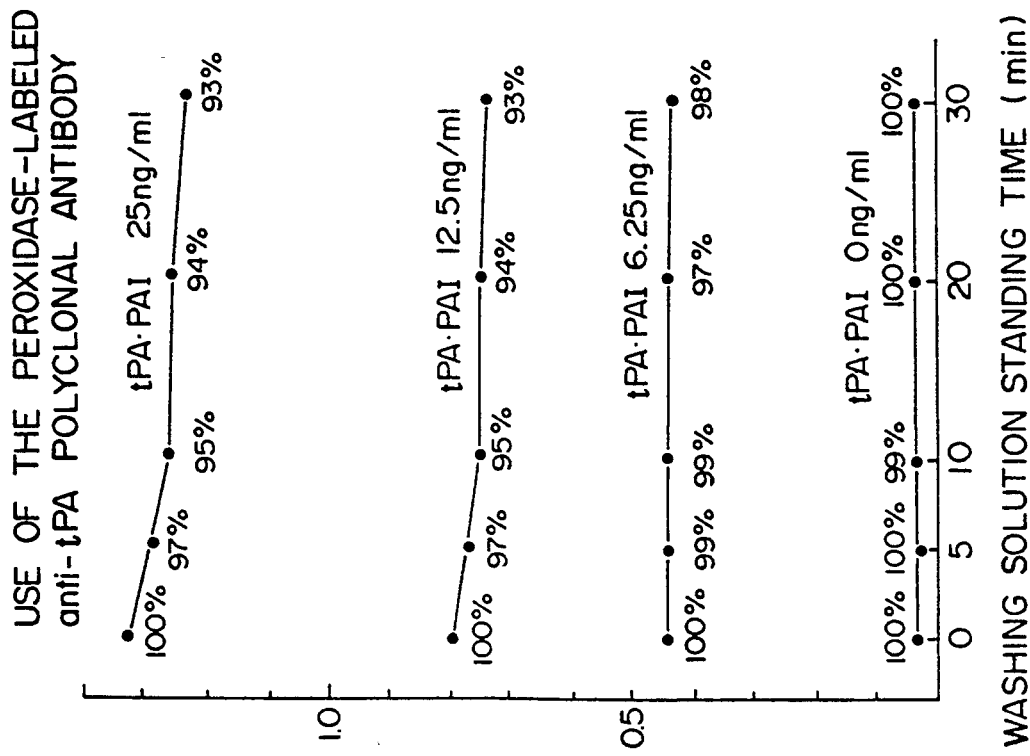

A human tPA-PAI complex was diluted with a 0.01M phosphate-0.5M NaCl-2% BSA buffer (pH 7.2) containing 0.25% skim milk to prepare 25, 12.5, 6.25 and 0 ng/ml solutions. 0.4 ml portions of the solutions of each concentration and the mouse anti-PAI antibody-immobilized beads prepared in Example 1 [Preparation of immobilized antibody] were placed in small test tubes, followed by incubation at 37° C. for 1 hour. After twice washing with a washing solution containing 0.05% TWEEN 20 in PBS, adjustment was made using a PBS-0.05% TWEEN 20 solution so that the concentration of the peroxidase labeled anti-tPA polyclonal antibody obtained in Example 1 or the peroxidase-labeled mouse anti-tPA antibody Fab' fragment becomes 1 μg/ml, 0.4 ml portions thereof were placed in the small test tubes, followed by incubation at 37° C. for 30 minutes. After two times washing with the washing solution, 3 ml portions of the washing solution were placed in the small test tubes, and after allowing the mixtures to stand for 0, 15, 20 and 30 minutes the washing solution was suction removed by an aspirator. Then, 0.4 ml portions of a peroxidase substrate (the same as in Example 1) were added, color was developed for 30 minutes, color development was stopped with 1N sulfuric acid, and absorbance was measured at 450 nm. The relation between the standing time after the addition of the washing solution and absorbance is shown in FIGS. 2a and b. FIG. 2a shows that when the peroxidase-labeled anti-tPA polyclonal antibody was used, the decrease of absorbance is small and the influence by the time required for the washing operation was insignificant.

EXAMPLE 3

Figure 3:
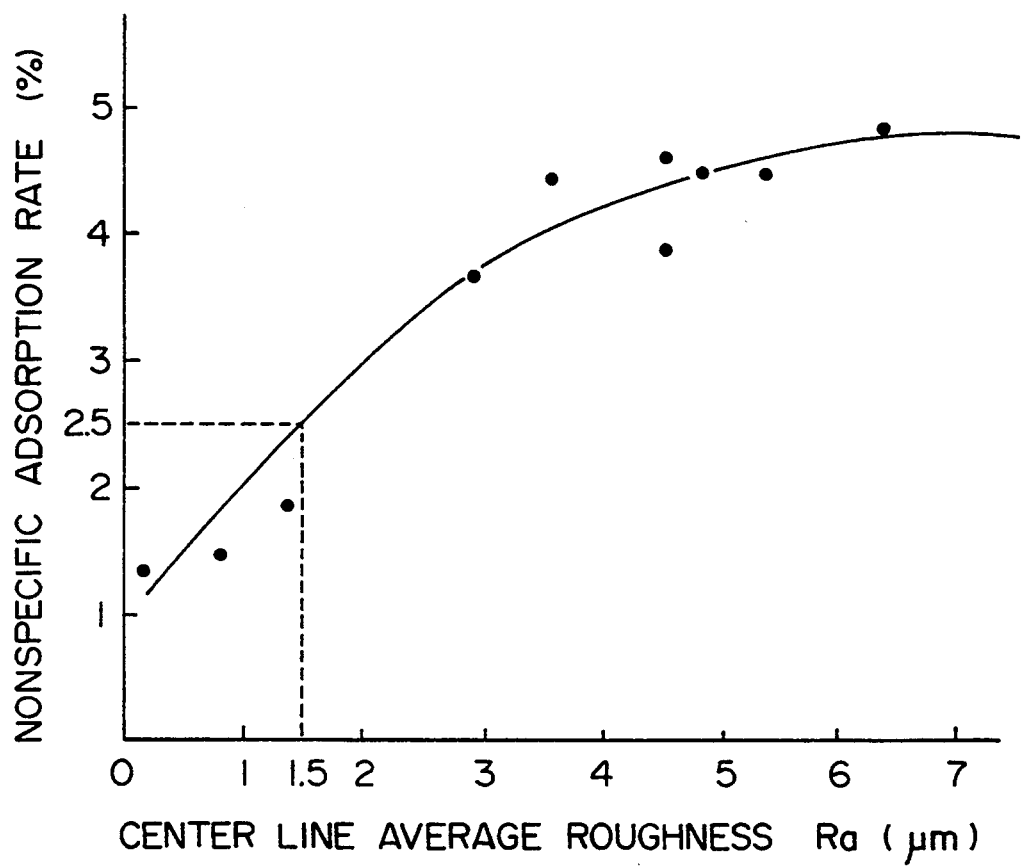
FIG. 3 denotes a relationship between the degree of the surface roughness of the insoluble solid carrier and nonspecific adsorption rate in the immunological assay of the tPA-PAI complex.

Several kinds of polystyrene beads having a diameter of 6.35 mm and different surface roughness were treated in the same manner as in "Preparation of immobilized antibody" in Example 1 to obtain several kinds of mouse anti-PAI antibody-immobilized beads. A solution containing a human tPA-PAI complex by 0 and 25 mg/ml was prepared with a 0.25% skim milk-0.01M phosphate-0.5M NaCl-2% BSA buffer. 0.4 ml portions of the solutions of each concentration and the plural kinds of mouse anti-PAI antibody-immobilized beads having a different surface roughness were placed in small test tubes, followed by incubation at 37° C. for 1 hour. Washing was made twice with a washing solution containing 0.05% TWEEN 20 in PBS. TWEEN TM is a trademark for a series of general-purpose emulsifiers and surface active agents. They are polyoxyethylene derivatives of fatty acid partial esters of sorbitol anhydrides. 0.4 ml portions of the solution of the peroxidase-labeled anti-tPA polyclonal antibody in PBS-0.05% TWEEN 20 (1 μg/ml) obtained in Example 1 were placed in the small test tubes, followed by incubation at 37° C. for 30 minutes. After washing was made three times with the washing solution, 0.4 ml portions of the substrate solution for peroxidase were added, color was developed at 37° C. for 30 minutes, color development was stopped with 1N sulfuric acid, and absorbance was measured at 450 mm. Nonspecific adsorption rate [(absorbance at 0 ng/ml/absorbance at 25 ng/ml)×100] was determined from the obtained absorbance. The surface roughness of the polystyrene beads was measured by a surface roughness tester Surfcom® (TOKYO SEIMITSU CO., LTD.). When the nonspecific adsorption rate and the center line average roughness (Ra) as a measure of surface roughness are taken as the longitudinal axis and horizontal axis respectively, FIG. 3 is obtained, and it is seen from the figure that the smaller the surface roughness is, the smaller the nonspecific adsorption becomes. When the nonspecific adsorption rate was 2.5% or less, the center line average roughness was 1.5 μm or less.

EXAMPLE 4

The absorbance values at tPA-PAI concentrations of 0 ng/ml (N) and 25 ng/ml (S) and their ratio (S/N) are denoted when solutions of the various surfactants in Table 1 in physiological saline were used as the washing solution in "Making of calibration curve" in Example 1. When the S/N ratio of 40 is supposed to be the allowable limit of nonspecific absorbance, the use of the nonionic surfactants having an HLB of 16 or more is effective for the inhibition of nonspecific adsorption, as is shown in Table 1. However, P-8P and TWEEN 40, nonionic surfactants having an HLB of 16 or less inhibited nonspecific adsorption but inhibited at the same time the specific reaction (S), and was not effective for highly sensitive analysis.

TABLE 1

| | | | | Absorbance | | |
|---|---|---|---|---|---|---|
| | | | Concentration | tPA.PAI | tPA.PAI | |
| Number | Surfactant | HLB | (w/w) % | (0 ng/ml) (N) | (25 ng/ml) (S) | S/N ratio |
| 1 | TWEEN 20 TM | 16.7 | 0.1% | 0.022 | 1.015 | 46.1 |
| 2 | TWEEN 20 TM | 16.7 | 0.05% | 0.022 | 1.185 | 53.9 |
| 3 | TWEEN 20 TM | 16.7 | 0.01% | 0.025 | 1.226 | 49.0 |
| 4 | PLURONIC F63 TM | 29.0 | 0.05% | 0.023 | 1.203 | 52.3 |
| Comparative Example | | | | | | |
| 1 | P-8P | 14.0 | 0.05% | 0.025 | 0.895 | 35.8 |
| 2 | TWEEN 40 | 15.6 | 0.05% | 0.027 | 0.957 | 35.4 |
| 3 | No addition | — | 0 | 0.122 | 1.235 | 10.1 |
| 4 | SDS | 40 | 0.05% | 0.022 | 0.135 | 6.1 |

EXAMPLE 5

[Inhibition of nonspecific adsorption with the addition of skim milk]

(a) Effect of skim milk addition to the first reaction solution

A human tPA-PAI complex was diluted with 0.01M PB-0.5M NaCl-2% BSA (pH 7.2) buffers containing 0, 0.01, 0.125, 0.25, 0.5, 0.8 and 1.0% skim milk respectively to prepare 0 and 25 ng/ml solutions. 0.4 ml portions of each solution and the mouse anti-PAI antibody-immobilized beads were placed in small test tubes, followed by incubation at 37° C. for 1 hour. Washing was then made twice with a washing solution containing 0.05% TWEEN 20 in PBS. A solution of 1 µg/ml the peroxidase-labeled anti-tPA polyclonal antibody in a BPS-0.05% TWEEN 20 solution was prepared, and 0.4 ml portions thereof were placed in the small test tubes, followed by incubation at 37° C. for 30 minutes. Washing was made three times with the washing solution, 0.4 ml portions of the substrate solution for peroxidase were added, color was developed at 37° C. for 30 minutes color development was stopped with 1N sulfuric acid, and absorbance at 450 nm was measured. The results are shown in Table 2a. It is seen that when the S/N ratio between the nonspecific adsorption (N) and the specific reaction (S) of 40.0 is supposed to be an allowable limit, an effective skim milk concentration range is 0.01 to 0.8%.

(b) Effect of skim milk addition to the second reaction solution

A human tPA-PAI complex was diluted with a 0.01M-PB-0.5M NaCl-2% BSA (pH 7.2) buffer containing 0.25% skim milk to prepare 0 and 25 ng/ml solutions. 0.4 ml portions of each solution and the mouse anti-PAI antibody solid beads were placed in small test tubes, followed by incubation at 37° C. for 1 hour. Then, washing was made twice with a washing solution containing 0.05% TWEEN ™ 20 in PBS. Solutions in PBS-0.05% TWEEN 20 containing the peroxidase-labeled anti-tPA polyclonal antibody at a concentration of 1 µg/ml and containing respectively 0, 0.01, 0.25, 0.5, 0.8 and 1.0% skim milk were prepared, and 0.4 ml portions thereof were placed in the small test tubes, followed by incubation at 37° C. for 30 minutes. After washing three times with the washing solution, 0.4 ml portions of the substrate for peroxidase were added, color was developed at 37° C. for 30 minutes, color development was discontinued with 1N sulfuric acid, and absorbance at 450 nm was measured. The results are shown in Table 2b. The S/N ratio based on the nonspecific adsorption (N) and the specific reaction (S) increases by the addition of skim milk by 0.01 to 0.8% and skim milk is seen to be effective.

TABLE 2a

Inhibition of nonspecific adsorption by skim milk addition

| Number | Skim milk concentration (%) | Absorbance tPA.PAI 0 ng/ml(N) | tPA.PAI 25 ng/ml(S) | S/N |
|---|---|---|---|---|
| 1 | 0 | 0.185 | 1.390 | 7.5 |
| 2 | 0.002 | 0.033 | 1.388 | 42.0 |
| 3 | 0.01 | 0.026 | 1.388 | 53.4 |
| 4 | 0.125 | 0.025 | 1.361 | 54.4 |
| 5 | 0.25 | 0.023 | 1.328 | 57.7 |
| 6 | 0.5 | 0.023 | 1.320 | 57.4 |
| 7 | 0.8 | 0.024 | 1.201 | 50.0 |
| 8 | 1.0 | 0.026 | 0.936 | 36.0 |

TABLE 2b

Inhibition of nonspecific adsorption by skim milk addition

| Number | Skim milk concentration (%) | Absorbance tPA.PAI 0 ng/ml(N) | tPA.PAI 25 ng/ml(S) | S/N |
|---|---|---|---|---|
| 1 | 0 | 0.023 | 1.328 | 57.7 |
| 2 | 0.002 | 0.023 | 1.320 | 59.4 |
| 3 | 0.01 | 0.022 | 1.315 | 59.8 |
| 4 | 0.125 | 0.021 | 1.261 | 66.0 |
| 5 | 0.25 | 0.021 | 1.245 | 59.3 |
| 6 | 0.5 | 0.021 | 1.240 | 29.0 |
| 7 | 0.8 | 0.021 | 1.050 | 50.0 |
| 8 | 1.0 | 0.024 | 0.953 | 39.7 |

EXAMPLE 6

[Assay of specimens from normal persons and patients]

Assay was carried out using 4-fold dilutions of plasmas from 5 normal persons and 3 patients of thrombosis in Example 1 [Making of calibration curve], and the results are shown in Table 3.

TABLE 3

Assay results on the specimens from normal persons and thrombosis patients

| | tPA.PAI complex concentration (ng/ml) |
|---|---|
| Normal person | |
| 1 | 4.0 |
| 2 | 7.2 |
| 3 | 8.9 |
| 4 | 7.2 |
| 5 | 7.0 |
| Patient | |
| 1 | 38.5 |
| 2 | 50.0 |
| 3 | 19.5 |

It is seen that the tPA-PAI complex concentrations in the thrombosis patients clearly exhibit high values and tPA-PAI complex concentration can be a marker in the prophylaxis of thrombosis.

EXAMPLE 7

[Assay of active PAI concentration]

A human tPA solution (0.5 µg/ml, 50 µl) was added to plasmas (each 50 µl) from normal persons and thrombosis patients, followed by incubation at 37° C. for 30 minutes. Thereafter, the concentration of the tPA-PAI complex was determined (result A) according to the making of a calibration curve in Example 1. At the same time, there were determined (result B) the concentrations of the human tPA-PAI complex in the plasmas from the normal persons and the thrombosis patients to which tPA was not added according to the making of calibration curve in Example 1. The concentration of the active PAI was determined by calculating the difference of both assayed values and making molecular weight conversion of PAI (result C). The results are shown in Table 4.

TABLE 4

| | tPA.PAI complex concentration | | (unit: ng/ml) Active PAI Result C |
|---|---|---|---|
| Specimen | Result A (tPA addition) | Result B (PA no addition) | concentration* |
| Normal person | | | |
| 1 | 11.4 | 4.0 | 3.1 |
| 2 | 23.4 | 7.2 | 6.8 |

TABLE 4-continued

|  | tPA.PAI complex concentration | | (unit: ng/ml) Active PAI Result C concentration* |
|---|---|---|---|
| Specimen | Result A (tPA addition) | Result B (PA no addition) |  |
| 3 | 8.0 | 4.2 | 1.6 |
| Thrombosis patient | | | |
| 1 | 69.0 | 38.5 | 12.8 |
| 2 | 101.0 | 50.1 | 21.4 |
| 3 | 98.0 | 19.5 | 33.0 |

*Active PAI concentration (Result A − Result B) × 0.42**

$$**0.42 = \frac{\text{PAI molecular weight (50,000)}}{\text{tPA—PAI molecular weight (120,000)}}$$

The active PAI concentrations in the thrombosis patients are significantly higher than those in the normal persons, and it was demonstrated that active PAI concentration can be a prophylactic marker on thrombosis.

We claim:

1. A method for an immunological assay of a human tissue plasminogen activator-human plasminogen activator inhibitor complex in a human specimen by:
   (1) contacting the human specimen with a first antibody linked to an insoluble solid carrier, and then contacting a labeled second antibody therewith, or
   (2) simultaneously contacting a first antibody linked to an insoluble solid carrier and a labeled second antibody with the human specimen, steps (1) and (2) being performed in the presence of a surfactant,
   (3) and, following step (1) or (2), measuring said labeled second antibody bound to said solid carrier to determine the human tissue plasminogen activator-human plasminogen activator inhibitor complex in the human specimen, which method comprises:
      (a) using as the first antibody a monoclonal antibody which specifically binds a human plasminogen activator inhibitor JTI-4 produced by the hybridoma JTI-4 (FERM BP-2318) linked onto an insoluble solid carrier having a specular surface,
      (b) using as the second antibody a polyclonal antibody which specifically binds a human tissue plasminogen activator labeled with an enzyme, and
      (c) said surfactant being a nonionic surfactant having an HLB (Hydrophilic-Lipophilic Balance) value of at least 16 and a concentration of 0.001–0.1 w/w %, said nonionic surfactant being at least one member selected from the group consisting of polyoxyalkylene alkyl aryl ether series, polyoxyalkylene alkyl ether series, polyoxyalkylene polyhydric alcohol fatty acid ester series and polyoxyethylene polyoxypropylene polyol series.

2. The method for the immunological assay of claim 1 which comprises contacting the human specimen with the first antibody linked to the insoluble solid carrier, and then contacting with the labeled second antibody.

3. The method for the immunological assay of claim 1 or 2 wherein a nonspecific adsorption inhibiting protein having a molecular weight of about 16,000 to about 50,000 and an isoelectric point of 1.0 to 5.0 contained in the second antibody and/or a diluent is further contacted such that the final concentration of said protein in the immune reaction solution is adjusted to 0.02–0.9% by weight.

4. The method for the immunological assay of claim 1 or 2 wherein the insoluble solid carrier is a polystyrene bead having a specular surface.

5. The method for the immunological assay of claim 3 wherein the protein is casein.

6. An immunological assay for active human plasminogen activator inhibitor which comprises:
   (1) providing two aliquots of a human specimen containing (i) a human tissue plasminogen activator-human plasminogen activator inhibitor complex and (ii) active human plasminogen activator inhibitor,
   (2) adding a sufficient amount of free human tissue plasminogen activator to one of the two aliquots to complex the active human plasminogen activator inhibitor,
   (3) contacting both the aliquots individually with a first antibody linked to an insoluble solid carrier, and then contacting a labeled second antibody therewith, or
   (4) simultaneously contacting the first antibody linked to the insoluble solid carrier and the labeled second antibody with the aliquots individually,
   steps (3) and (4) being performed in the presence of a surfactant,
   (5) measuring solid phase bound label to determine the amount of human plasminogen activator-human tissue plasminogen activator inhibitor complex in each of the aliquots, and
   (6) determining the amount of active human plasminogen activator inhibitor based on the difference between the amount of human tissue plasminogen activator-human plasminogen activator inhibitor complex in the two aliquots,
   and wherein
      (a) there is used as the first antibody a monoclonal antibody JTI-4 produced by the hybridoma JTI-4 (FERM BP-2318) which specifically binds a human plasminogen activator inhibitor linked to an insoluble solid carrier having a specular surface,
      (b) there is used as the second antibody a polyclonal antibody which specifically binds a human tissue plasminogen activator labeled with an enzyme, and
      (c) there is used as the surfactant a nonionic surfactant having an HLB (Hydrophilic-Lipophilic Balance) of at least 16 and a concentration of 0.001–0.1 w/w %, said nonionic surfactant being at least one member selected from the group consisting of polyoxyalkylene alkyl aryl ether series, polyoxyalkylene alkyl ether series, polyoxyalkylene polyhydric alcohol fatty acid ester series and polyoxyethylene polyoxypropylene polyol series.

* * * * *